US010292758B2

(12) United States Patent
Boudreaux et al.

(10) Patent No.: US 10,292,758 B2
(45) Date of Patent: May 21, 2019

(54) METHODS AND DEVICES FOR ARTICULATING LAPAROSCOPIC ENERGY DEVICE

(71) Applicant: Ethicon Endo-Surgery, Inc., Cincinnati, OH (US)

(72) Inventors: Chad P. Boudreaux, Cincinnati, OH (US); Scott R. Bingham, Mason, OH (US); Matthew C. Miller, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 645 days.

(21) Appl. No.: 14/511,924

(22) Filed: Oct. 10, 2014

(65) Prior Publication Data

US 2016/0100882 A1 Apr. 14, 2016

(51) Int. Cl.
*A61B 18/14* (2006.01)
*A61B 18/00* (2006.01)
(Continued)

(52) U.S. Cl.
CPC ............ *A61B 18/1445* (2013.01); *A61B 2017/00314* (2013.01); *A61B 2017/2902* (2013.01); *A61B 2017/294* (2013.01); *A61B 2017/2929* (2013.01); *A61B 2017/2938* (2013.01); *A61B 2018/0063* (2013.01);
(Continued)

(58) Field of Classification Search
CPC ........ A61B 18/1445; A61B 2017/2929; A61B 2017/2927; A61B 2017/2937; A61B 2017/2932; A61B 2018/1445
See application file for complete search history.

(56) References Cited

U.S. PATENT DOCUMENTS

| 4,203,430 A | 5/1980 | Takahashi |
| 4,880,015 A | 11/1989 | Nierman |

(Continued)

FOREIGN PATENT DOCUMENTS

| DE | 4300307 A1 | 7/1994 |
| DE | 19703600 A1 | 8/1998 |

OTHER PUBLICATIONS

International Search Report for PCT Application No. PCT/US2015/053105 dated Mar. 31, 2016 (7 pages).

*Primary Examiner* — Jaymi E Della
(74) *Attorney, Agent, or Firm* — Mintz Levin Cohn Ferris Glovsky and Popeo, P.C.

(57) ABSTRACT

Electrosurgical instruments and associated methods are disclosed herein. Embodiments of the electrosurgical instruments can include an elongate shaft that can articulate an end effector relative to the elongate shaft, with the end effector including opposed jaws and positioned at a distal end of the elongate shaft. In addition, electrosurgical instruments are provided that include a cutting feature or knife that is coupled to the end effector and can axially translate relative to the elongate shaft. Furthermore, the knife can be rotated relative to the elongate shaft, which can cause simultaneous rotation of the end effector. Electrosurgical instruments are also provided that include an end effector including opposed jaws that are configured to rotate relative to the elongate shaft and grasp objects (i.e., via opening and closing the opposed jaws). Electrical energy can also be passed through the electrosurgical instrument for performing electrosurgical procedures.

20 Claims, 12 Drawing Sheets

(51) Int. Cl.
   *A61B 17/00* (2006.01)
   *A61B 17/29* (2006.01)
(52) U.S. Cl.
   CPC ............. *A61B 2018/00202* (2013.01); *A61B 2018/00607* (2013.01); *A61B 2018/1455* (2013.01)

(56) References Cited

U.S. PATENT DOCUMENTS

| | | | |
|---|---|---|---|
| 5,020,514 | A | 6/1991 | Heckele |
| 5,330,502 | A | 7/1994 | Hassler et al. |
| 5,350,391 | A | 9/1994 | Iacovelli |
| 5,607,450 | A | 3/1997 | Zvenyatsky et al. |
| 5,632,432 | A | 5/1997 | Schulze et al. |
| 5,860,995 | A * | 1/1999 | Berkelaar ............ A61B 17/29 606/174 |
| 5,921,956 | A | 7/1999 | Grinberg et al. |
| 6,162,208 | A | 12/2000 | Hipps |
| 6,299,625 | B1 * | 10/2001 | Bacher ............ A61B 17/2909 606/167 |
| 6,500,176 | B1 | 12/2002 | Truckai et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckal et al. |
| 7,381,209 | B2 | 6/2008 | Truckai et al. |
| 7,691,095 | B2 | 4/2010 | Bednarek et al. |
| 7,909,220 | B2 | 3/2011 | Viola |
| 8,767,970 | B2 | 7/2014 | Eppolito |
| 2008/0287741 | A1 * | 11/2008 | Ostrovsky .......... A61B 1/00071 600/141 |
| 2008/0300579 | A1 * | 12/2008 | Broehl ............ A61B 17/07207 606/1 |
| 2009/0084826 | A1 | 4/2009 | Shah et al. |
| 2009/0088792 | A1 * | 4/2009 | Hoell, Jr. ............... A61B 17/29 606/206 |
| 2010/0048999 | A1 * | 2/2010 | Boulais ............ A61B 1/00059 600/141 |
| 2011/0087218 | A1 | 4/2011 | Boudreaux et al. |
| 2011/0106078 | A1 | 5/2011 | Mueller |
| 2011/0125176 | A1 * | 5/2011 | Yates ............ A61B 17/07207 606/170 |
| 2011/0213360 | A1 * | 9/2011 | Cunningham ......... A61B 17/29 606/41 |
| 2011/0301604 | A1 * | 12/2011 | Horner .................. A61B 17/29 606/52 |
| 2011/0319888 | A1 * | 12/2011 | Mueller ............ A61B 18/1445 606/41 |
| 2012/0074200 | A1 | 3/2012 | Schmid et al. |
| 2012/0078243 | A1 * | 3/2012 | Worrell ............ A61B 17/07207 606/33 |
| 2012/0078248 | A1 * | 3/2012 | Worrell ............ A61B 18/1445 606/45 |
| 2012/0239009 | A1 * | 9/2012 | Mollere ............ A61B 17/07207 606/1 |

* cited by examiner

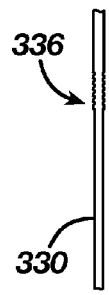
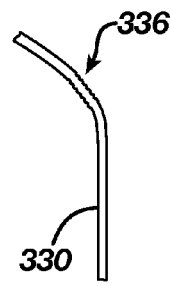
FIG. 10A    FIG. 10B
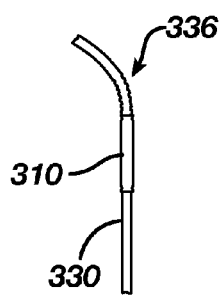
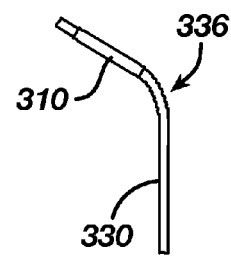
FIG. 10C    FIG. 10D
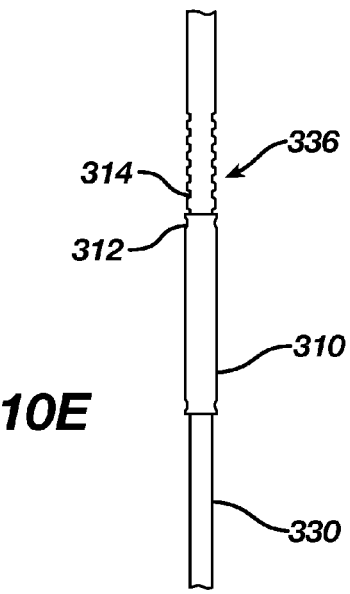
FIG. 10E

METHODS AND DEVICES FOR ARTICULATING LAPAROSCOPIC ENERGY DEVICE

FIELD

Articulating laparoscopic energy devices and associated methods are disclosed herein.

BACKGROUND

Laparoscopic surgery, which can also be referred to as minimally invasive surgery, is a surgical technique that includes operations performed through small incisions in the body of a patient. There can be a number of advantages to the patient with laparoscopic surgery compared to open procedures where larger incisions are made. For example, pain and hemorrhaging can be reduced due to the smaller incisions and recovery times can be shorter.

In a conventional laparoscopic procedure, a distal end of a laparoscopic or electrosurgical device can be passed through a small incision in the skin of a patient. The distal end of the laparoscopic device is then positioned at or adjacent a surgical site. One or more surgical procedures are then performed at the surgical site, which can include cutting and/or sealing tissue. The distal end of the laparoscopic device can be removed from the patient after the completion of the surgical procedure. Disadvantages present in conventional laparoscopic devices can include one or more limited abilities with respect to steering (i.e., positioning) the distal end of the laparoscopic device and manipulating of distal features of the laparoscopic device (e.g., clasping features, vessel sealing features, cutting features, etc.). Accordingly, a need exists for improved laparoscopic devices and associated methods.

SUMMARY

Various surgical instruments and methods are disclosed herein for performing laparoscopic surgery. In one embodiment, an electrosurgical device is provided and includes a handle assembly and an elongate shaft extending distally from the handle assembly and having an end effector with opposed jaws rotatably coupled to a distal end thereof at a rotational joint. The elongate shaft can include an articulation joint proximal of the rotational joint for allowing articulation of the end effector relative to the elongate shaft. The electrosurgical device can further include a closure assembly having a support housing with first and second closure bands extending therethrough. The first and second closure bands can extend through the elongate shaft and be operatively coupled to the end effector for moving the opposed jaws between open and closed positions. The support housing can be configured to allow the first and second closure bands to shift axially relative to one another within the support housing in response to articulation of the end effector about the articulation joint, and with the first and second closure bands in any shifted position, the support housing can be axially movable to simultaneously axially move the first and second closure bands and to cause the opposed jaws to move between the open and closed positions.

In some embodiments, the support housing can include a gimbal having an axial opening extending longitudinally therethrough for receiving the first and second closure bands. The support housing can also include vertical and horizontal cross bars disposed therein and coupled to one another with the vertical cross bar being configured to pivot to allow shifting movement of the first and second closure bands. The horizontal cross bar can be configured to move axially to simultaneously axially move with the first and second closure bands. The first and second closure bands can each include an opening formed in a proximal end thereof, and the horizontal cross bar can extend through the opening formed in each of the first and second closure bands. The support housing can include opposed elongate slots formed therein for receiving opposed ends of the horizontal cross bar such that the opposed ends of the horizontal cross bar can pivot within the elongate slots. The opposed ends of the vertical cross bar can be fixedly disposed within opposed holes formed in the support housing.

In certain embodiments, the electrosurgical device can further include an articulation assembly having an articulation mechanism that controls first and second articulation bands extending through the elongate shaft and operatively coupled to the end effector such that activation of the articulation mechanism causes axial movement of the first and second articulation bands, which is effective to articulate the end effector relative to the elongate shaft about the articulation joint. The articulation mechanism can further include an articulation knob disposed on the handle housing for causing axial movement of the first and second articulation bands. The electrosurgical device can further include an articulation control mechanism that can be disposed along the elongate shaft and slidably movable relative to the articulation joint to adjust a bending radius of the articulation joint. The electrosurgical device can further include an active rod extending along the elongate shaft and configured to provide electrical communication between a power source at a proximal end of the active rod and an electrode at a distal end of the active rod. The electrode can extends along a length of a first jaw of the opposed jaws.

In some embodiments, a method of articulating an electrosurgical device is provided. The method can include actuating an articulation knob on a handle housing of an electrosurgical device to cause an end effector coupled to a distal end of the elongate shaft to articulate about an articulation joint on the elongate shaft. Articulation of the end effector can cause first and second closure bands extending through the elongate shaft to shift in opposite directions relative to one another. The method can also include, with the end effector in an articulated position, actuating a closure member on the handle housing to cause the support housing to simultaneously axially move the first and second closure bands, which extend through the support housing and the elongate shaft, and to cause opposed jaws of the end effector to move between open and closed positions In other aspects, the method can include activating a power source coupled to the handle housing to cause electrical energy to be delivered to at least one jaw of the end effector.

In some embodiments, an electrosurgical device can include an elongate shaft having an end effector with opposed jaws rotatably coupled to a distal end thereof at a rotational joint, the elongate shaft including an articulation joint proximal of the rotational joint for allowing articulation of the end effector relative to the elongate shaft. The electrosurgical device can also include a knife assembly coupled to the end effector and including a knife at a distal end thereof configured to axially translate relative to the opposed jaws for cutting tissue engaged between the opposed jaws. The electrosurgical device can further include a knife positioning rod extending through the elongate shaft and coupled to the knife assembly, the knife positioning rod being axially translatable for causing the knife assembly to translate, and the knife positioning rod being rotatable relative to the elongate shaft to cause rotation of the end effector about the rotational joint. The electrosurgical device can include a knife advancing member coupled to the knife positioning rod for causing axial translation of the knife positioning rod relative to the elongate shaft, the knife advancing member being non-rotatable relative to the elongate shaft and allowing free rotational movement of the knife positioning rod relative thereto.

The knife positioning rod can include a cut-out formed therein for receiving a portion of the knife advancing member such that the knife advancing member is effective to cause axial translation of the knife positioning rod while allowing free rotational movement of the knife advancer shaft relative thereto. The knife rotating member can be coupled to the knife positioning rod and the knife rotating member can be axially rotatable relative to the elongate shaft to cause rotation of the end effector about the rotational joint. At least a portion of the knife positioning rod can be formed from a flexible braided tubing. The electrosurgical device can further include an active rod extending along the elongate shaft and configured to provide electrical communication between a power source at a proximal end of the active rod and an electrode at a distal end of the active rod. The electrode can extend along a length of a first jaw of the opposed jaws.

In some embodiments, a method of manipulating a knife of an electrosurgical device is provided. The method can include actuating a rotation knob on a handle housing of an electrosurgical device to cause a knife positioning rod extending through an elongate shaft of the device to rotate and thereby cause an end effector at a distal end of the elongate shaft to rotate about a rotational joint formed on the elongate shaft, the knife positioning rod extending through a non-rotatable knife advancing member. The method can also include actuating a closure member on the handle housing to cause opposed jaws of the end effector to engage tissue therebetween and actuating a firing member on the handle housing to cause the non-rotatable knife advancing member to axially translate to advance a knife along the end effector to thereby cut tissue captured between the opposed jaws.

In other aspects, the method can include actuating an articulation knob on the handle housing to cause the end effector to articulate about an articulation joint located proximal to the rotational joint. The method can also include activating a power source coupled to the handle housing to cause electrical energy to be delivered to at least one jaw of the end effector.

In some embodiments, an electrosurgical device is provided and includes an elongate shaft having an end effector with opposed jaws rotatably coupled to a distal end thereof at a rotational joint, the elongate shaft including an articulation joint proximal of the rotational joint for allowing articulation of the end effector relative to the elongate shaft. The electrosurgical device can further include a proximal pull tube extending through the elongate shaft proximal of the rotational joint, and a distal pull tube extending through the end effector distal of the rotational joint, the proximal pull tube being axially translatable along the elongate shaft to cause the distal pull tube to axially translate to open and close the opposed jaws, and the distal pull tube being configured to rotate freely relative to the proximal pull tube to allow rotation of the end effector about the rotational joint.

In certain embodiments, the electrosurgical device can further include a knife assembly extending through the end effector and including a knife for cutting tissue engaged between the opposed jaws, wherein rotation of the knife assembly is effective to cause rotation of the end effector about the rotational joint and to cause rotation of the distal pull tube relative to the proximal pull tube. The knife assembly can include a knife rotating member extending through the elongate shaft and coupled to a knife positioning rod having the knife positioned at a distal end thereof, the knife rotating member being axially rotatable relative to the elongate shaft to cause rotation of the knife assembly and end effector.

In some embodiments, a method of manipulating an end effector of an electrosurgical device is provided. The method can include actuating a rotation member on an electrosurgical device to cause a knife rotating member extending through an elongate shaft of the device to rotate, rotation of the knife rotating member causing an end effector coupled to the elongate shaft to rotate about a rotational joint, and to cause rotation of a distal pull tube coupled to the end effector and positioned distal of the rotational joint. The method can further include actuating a closure member on the electrosurgical device to cause axial translation of a proximal pull tube extending through the elongate shaft proximal of the rotational joint knife to axially translate along the elongate shaft, axial translation of the proximal pull tube causing the distal pull tube to axially translate and thereby open and close the opposed jaws.

In other aspects, the method can include actuating an articulation mechanism on the device to cause the end effector to articulate about an articulation joint located proximal of the rotational joint. The distal pull tube can be freely rotatably mated to the proximal pull tube such that the distal pull tube rotates during actuation of the rotation member while the proximal pull tubes remains stationary.

The present disclosure further provides devices and methods as claimed.

BRIEF DESCRIPTION OF THE DRAWINGS

The invention will be more fully understood from the following detailed description taken in conjunction with the accompanying drawings, in which:

FIG. 10A is a side view of another embodiment of a shaft of an electrosurgical instrument in a straight configuration, with the shaft including surface features for enabling engagement and positioning of a sheath;

FIG. 10B is a side view of the shaft shown in FIG. 10A in an articulated configuration;

FIG. 10C is a side view of the shaft shown in FIG. 10A in an articulated configuration with the sheath positioned along a proximal end of an articulation section of the shaft;

FIG. 10D is a side view of the shaft shown in FIG. 10A in an articulated configuration with the sheath positioned along a distal end of the articulation section of the shaft;

FIG. 10E is a side view of the shaft shown in FIG. 10A in a straight configuration with the sheath positioned along a proximal end of the articulation section of the shaft and showing detent features of the shaft engaged with the surface features of the shaft;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Methods and devices for performing laparoscopic procedures are provided herein. Laparoscopic procedures allow for smaller incisions, which can result in less painful and faster recoveries for patients who undergo such procedures. In general, laparoscopic devices or electrosurgical instruments are described herein that include an elongate shaft that can articulate an end effector relative to the elongate shaft, with the end effector including opposed jaws and being positioned at a distal end of the elongate shaft. In addition, electrosurgical instruments are provided that include a cutting feature or knife that is coupled to the end effector and that can axially translate relative to the elongate shaft and end effector. Furthermore, the knife can be rotated relative to the elongate shaft, which can cause simultaneous rotation of the end effector. Electrosurgical instruments are also provided that include an end effector having opposed jaws that are configured to rotate relative to the elongate shaft and grasp objects (i.e., via opening and closing the opposed jaws). Electrical energy can also be passed through the electrosurgical instrument for performing electrosurgical procedures.

Figure 1:
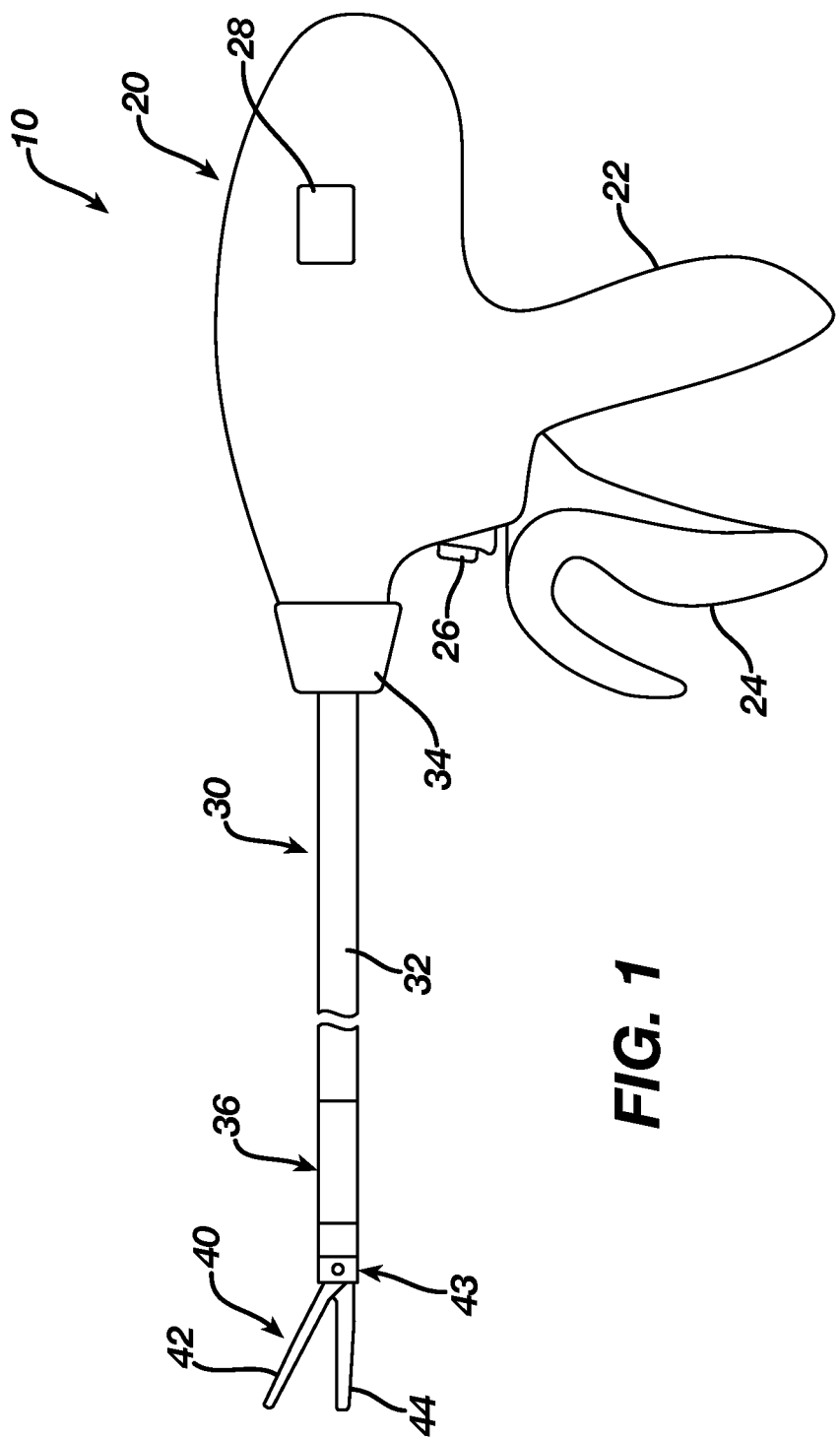
FIG. 1 is a side view of one embodiment of an electrosurgical instrument including a shaft an end effector positioned at a distal end of the shaft.

FIG. 1 shows one embodiment of an electrosurgical device or instrument 10 that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218; and/or U.S. patent application Ser. No. 13/151,181, each of which is incorporated herein by reference in its entirety. As described therein and as will be described in greater detail below, the electrosurgical instrument 10 is operable to cut tissue and seal or weld tissue (e.g., a blood vessel, etc.), including substantially simultaneously. In other words, the electrosurgical instrument 10 operates similar to an endocutter type of stapler, except that electrosurgical instrument 10 provides tissue welding through application of bipolar RE energy instead of providing lines of staples to join tissue. It should also be understood that the electrosurgical instrument 10 may have various structural and functional similarities with the ENSEAL® Tissue Sealing Device by Ethicon Endo-Surgery, Inc., of Cincinnati, Ohio. Furthermore, the electrosurgical instrument 10 may have various structural and functional similarities with the devices taught in any of the other references that are cited and incorporated by reference herein.

As shown in FIG. 1, the electrosurgical instrument 10 can include a handle assembly or handpiece 20, a shaft 30 extending distally from handpiece 20, and an end effector 40 disposed at a distal end of shaft 30. The illustrated handpiece 20 includes a pistol grip 22, a pivoting trigger 24, an activation button 26, and an articulation control 28. The trigger 24 can be pivotable toward and away from the pistol grip 22 to selectively actuate the end effector 40 as will be described in greater detail below. The activation button 26 can be operable to selectively activate RF circuitry that is in communication with the end effector 40, as will also be described in greater detail below. In some versions, the activation button 26 can also serve as a mechanical lockout against the trigger 24, such that the trigger 24 cannot be fully actuated unless the button 26 is being pressed simultaneously. Examples of how such a lockout may be provided are disclosed in one or more of the references cited herein. It should be understood that the pistol grip 22, trigger 24, and button 26 may be modified, substituted, supplemented, etc. in any suitable way, and that the descriptions of such components herein are merely illustrative. The articulation control 28 can be operable to selectively control an articulation section 36 of the shaft 30, which will be described in greater detail below. Various examples of forms that the articulation control 28 may take will also be described in greater detail below, while further examples will be apparent to those of ordinary skill in the art in view of the teachings herein. In addition, the handpiece 20 can include a variety of features for manipulating the electrosurgical device, such as jaw control features (not shown) for opening and closing opposing jaws of the end effector 40. Additionally, the handpiece 20 can include a variety of features for manipulating the electrosurgical device, such as knife assembly control features (not shown) for advancing, retracting and rotating a knife of the knife assembly relative to the shaft 30 of the electrosurgical device.

The shaft 30 of the present example can include an outer sheath 32 and an articulation section 36. The articulation section 36 can be operable to selectively position the end effector 40 at various angles relative to the shaft 30 or longitudinal axis defined by the outer sheath 32. Various examples of forms of the articulation section 36 and other components of the shaft 30 will be described in greater detail below, while further examples will be apparent to those of ordinary skill in the art in view of the teachings herein. For instance, it should be understood that various components that are operable to actuate the articulation section 36 may extend through the interior of the sheath 32. In some versions, the shaft 30 can also include a rotational joint that is positioned distal to the articulation section 36 and proximal to the end effector 40, as will be described in greater detail below. In addition, the end effector 40 can include any part of the electrosurgical instrument 10 that is distal to the rotational joint. The rotational joint can allow the end effector 40 to rotate relative to the shaft. For example, rotation of the end effector 40 can be activated by one or more features associated with the handpiece. In some other versions, a knob 34 associated with the handpiece 20 can be operable to rotate end effector 40 without rotating any portion of the shaft 30, such as any portion of the electrosurgical instrument 10 that is proximal to either the rotational joint or the articulation section 36. As another merely illustrative example, the electrosurgical instrument 10 can include one rotation control that provides rotatability of the shaft 30 and end effector 40 as a single unit; and another rotation control that provides rotatability of end effector 40 without rotating any portion of shaft 30 that is proximal to either the rotational joint or articulation section 36. Other suitable rotation schemes will be apparent to those of ordinary skill in the art in view of the teachings herein. Of course, rotatable features may simply be omitted if desired.

Figure 2A:
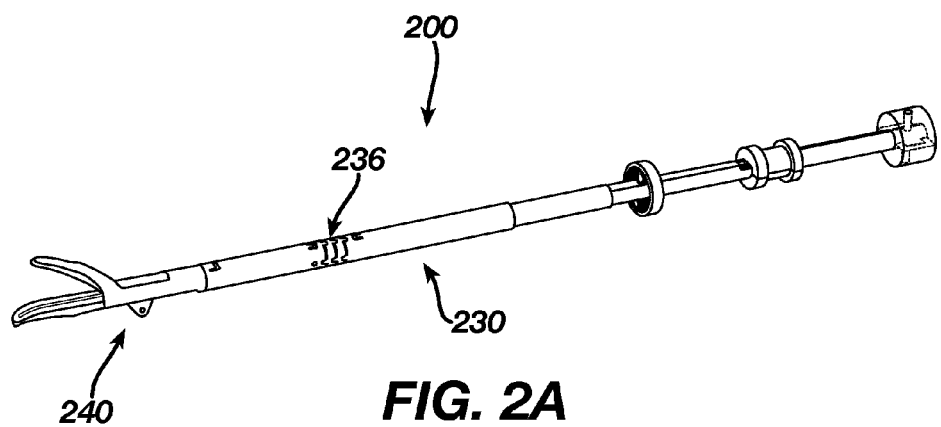
FIG. 2A is a side perspective view showing multiple mechanisms of another embodiment of the electrosurgical instrument, the mechanisms including an articulation mechanism, an end effector manipulation mechanism, and a knife translating and rotating mechanism.
Figure 2B:
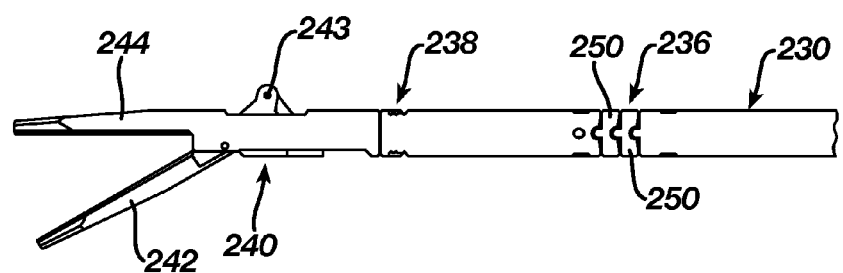
FIG. 2B is a side view of a distal end of the electrosurgical instrument shown in FIG. 2A showing a distal portion of a shaft and an end effector positioned at a distal end of the shaft, with the end effector including opposing jaws.

FIGS. 2A and 2B illustrate one embodiment of an electrosurgical instrument 200 showing a part of a shaft 230 that can extend from a handpiece, such as the handpiece 20 shown in FIG. 1. A distal end of the shaft 230 can include an end effector 240 having a pair of opposed jaws. The opposed jaws can include a first jaw 242 and a second jaw 244, with the second jaw 244 substantially fixed relative to the shaft 230. The first jaw 242 can pivot relative to the shaft 230, such as toward and away from the second jaw 244. A person skilled in the art will appreciate that either or both of the jaws 242, 244 can be pivotally movable. The jaws 242, 244 can be elongate in shape, which can allow them to accept and capture tissue therebetween. In addition, the jaws 242, 244 can have a variety of features along their opposing inner surfaces, such as grasping features (e.g., teeth, etc.) for securing captured tissue. The first jaw 242 and second jaw 244 can have the same or similar shapes and/or features. However, the first jaw 242 and second jaw 244 can have different shapes and/or features that allow them to assist with a variety of surgical procedures and are not limited to the configurations shown or described herein. In addition, one or more of the components shown at or adjacent the proximal end of shaft 230, as shown in FIG. 2A, can be enclosed within the handpiece for allowing a user to manipulate one or more controls associated with the handpiece that can control these one or more components, which can include any part of the articulation assembly, closure assembly, and knife assembly that will be described in greater detail below In some embodiments, the first jaw 242 can be pivotally coupled to a jaw activation mechanism or closure assembly, which can include a joint or pivotal coupling 243 that can be activated to cause the first jaw 242 to open or close relative to the second jaw 242, as will be described in greater detail below. Alternatively or in addition, actuators such as rods, bands or cables, etc., may extend through the shaft 230 and be joined with the first jaw 242 at the pivotal coupling 243, such that longitudinal movement of the actuator rods/bands/cables/etc. through the shaft 230 can provide pivoting of the first jaw 242 relative to the second jaw 244. The first jaw 242 and the second jaw 244 can be configured for any suitable kind of movement and may be actuated in any other suitable fashion.

As shown in FIGS. 2A and 2B, the electrosurgical instrument 200 can have an elongated tubular shaped shaft 230 that can include an articulation section 236 adjacent the distal end of the shaft 230. The articulation section 236 can include one or more articulation joints 250 that can allow the shaft 230 to articulate along the articulation section 236, such as by activating an articulation knob disposed on the handpiece. The articulation section 236 can be proximal to a rotational joint 238 that allows the end effector 240 to rotate relative to the shaft 230. The end effector 240 can be defined, for example, as anything distal to the rotational joint 238. Activation of the articulation section 236 can cause the end effector 240 to form an angle relative to the shaft 230. For example, articulation at the articulation section 236 can assist the distal end of the electrosurgical instrument 200, such as the end effector 240, with navigating to a surgical site.

Figure 3A:
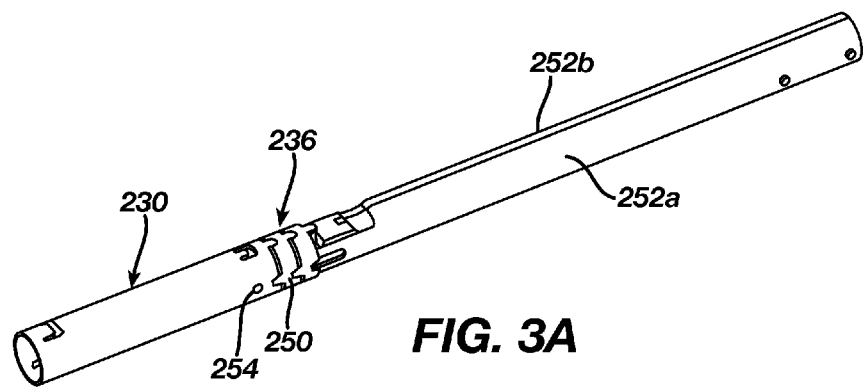
FIG. 3A is a side perspective view of a part of the articulation mechanism of the electrosurgical instrument shown in FIG. 2A, including a distal end of the shaft, an articulation section and first and second articulation bands.
Figure 3B:
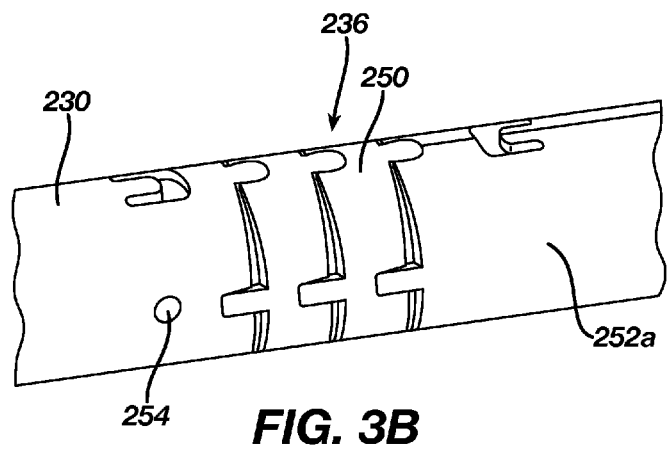
FIG. 3B is a partial view of the articulation section showing a distal end of one of the articulation bands attached to a part of the distal end of the shaft.

FIGS. 3A and 3B show a part of the articulation mechanism of the electrosurgical instrument 200, which can include the articulation section 236 having one or more articulation joints 250. FIGS. 3A and 3B further illustrates the distal end of the shaft 230 and elongated first and second articulation bands 252a, 252b extending proximally from the articulation section 236. The articulation joints 250 can be made by laser-cutting circumferential patterns along a part of the elongated tubular shaft 230. The articulation joints 250 can allow the shaft 230 to articulate in a variety of ways, including forming various angles between the end effector 240 and the shaft 230 and forming various radii bends along the articulation section 236. This can allow the electrosurgical instrument 200 to adapt to a variety of navigating circumstances.

Articulation of the articulation section 236 can be caused by either pushing or pulling on one or more of the articulation bands 252a, 252b that extend through an internal lumen of the shaft 230. For example, the articulation bands 252a, 252b can be attached or joined to a part of the shaft 230 distal to the articulation section 236, such as at attachment point 254 shown in FIGS. 3A and 3B. In some implementations, a first articulation band 252a can be positioned on one side of the inner wall of the shaft 230 and a second articulation band 252b can be positioned on an opposing side of the shaft 230 from the first articulation band 252a. As such, pushing on the first articulation band 252a and pulling on the opposing second articulation band 252b can cause articulation of the shaft 230 along the articulation section 236. For example, pushing on articulation band 252a and pulling articulation band 252b can cause the end effector to move in a direction toward a side having articulation band 252b extending therealong. Positioning of the articulation bands 252a, 252b can vary and are not limited to a pair of articulation bands 252a, 252b positioned along opposing sides of the inner wall of the shaft 230. In addition, each articulation band 252a, 252b can include more than one extension or more than one band in order to allow for multiple attachments between each of the articulation bands 252a, 252b with various parts comprising the electrosurgical instrument 200. Furthermore, the articulation bands 252a, 252b can be made out of one or more of a variety of materials, including a variety of flexible materials.

FIGS. 4A-4D show a part of the end effector manipulation mechanism or closure assembly of the electrosurgical instrument 200, which can include first and second closure bands 253a, 253b each having a proximal end 256 coupled to an closure mechanism 260 and a distal end coupled to a distal component of the shaft 230, e.g., proximal pull tube 274. The closure mechanism 260 can include a support housing 261 having an axial opening extending longitudinally therethrough. The housing 261 can be cylindrical in shape; however, the housing 261 can have any number of shapes and sizes. The support housing 261 can receive proximal ends of the closure bands 253a, 253b and can include a gimbal having a vertical bar 264 and a horizontal bar 262 positioned within the housing 261. In addition, the vertical bar 264 and the horizontal bar 262 can be coupled to one another. The vertical bar 264 can be disposed within opposed vertical holes 265 in the housing 261, which can allow the vertical bar 264 to pivot or rotate within the opposed holes 265, while holding the vertical bar 264 in a substantially fixed longitudinal position. The horizontal bar 262 can be disposed within opposing elongate slots 268 that can allow the horizontal bar 262 to shift axially in the direction of the longitudinal axis of the shaft 230, such as when the vertical bar 264 pivots within the opposed holes 265.

Figure 4A:
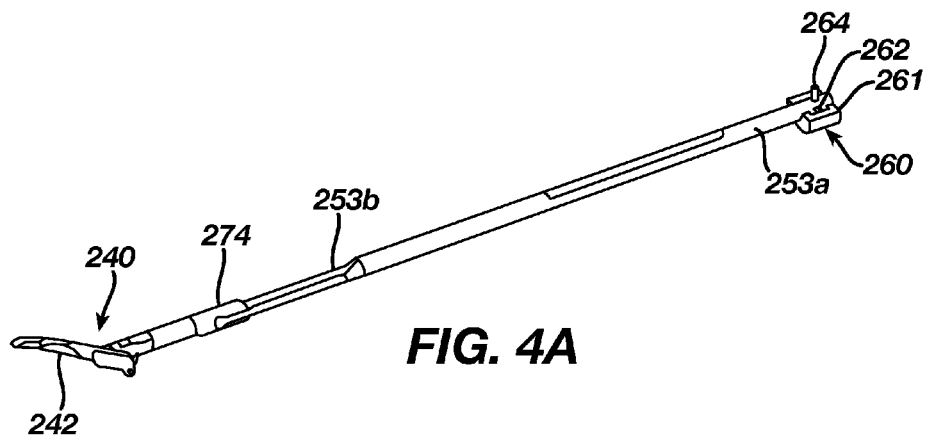
FIG. 4A is a side perspective view of a distal portion of the electrosurgical instrument shown in FIG. 2A, including a support housing and first and second closure bands that extend between a proximal pull tube and the support housing.
Figure 4B:
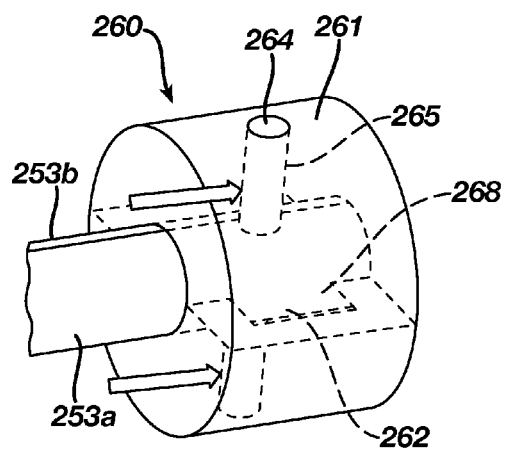
FIG. 4B is a side perspective view of the support housing shown in FIG. 4A.
Figure 4C:
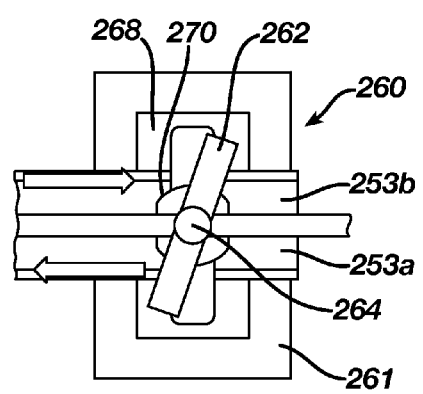
FIG. 4C is a cross-sectional view of the support housing shown in FIG. 4B.

Movement of the vertical bar 264 and horizontal bar 262 can be caused by movement of one or more of the closure bands 253a, 253b extending through the housing 261. For example, each closure bands 253a, 253b can extend longitudinally through the housing 261 and can include an opening 270 configured to allow an end of the horizontal bar 262 to extend therethrough, which allows the horizontal bar 262 to engage the closure bands 253a, 253b. As such, when the closure bands 253a, 253b move in opposite directions relative to the housing 261, the horizontal bar 262 can be forced to shift within the opposing elongate slots 268 (i.e., via pivot of the vertical bar 264), which can also allow opposing movements of the closure bands 253a, 253b within the housing 261, as shown in FIG. 4C.

For example, as discussed above, movement of a first articulation band 252a in a first direction and movement of a second articulation band 252b in a direction opposite the first direction can cause articulation of the end effector 240 (e.g., via bending about the articulation section 236). As such, the closure bands 253a, 253b can also be caused to shift or move in opposite directions relative to each other due to the closure bands 253a, 253b conforming to the bending along the articulation section 236 of which they extend along. The horizontal bar 262 can move in opposite directions in coordination with the closure bands 253a, 253b moving in opposite directions relative to each other. As such, with the horizontal bar 262 in any shifted position, a force can be applied from the closure mechanism 260, which can be evenly distributed to the closure bands 253a, 253b. This allows linear translation of the closure mechanism 260 to cause the jaws 242, 244 to open and close as a result of force transferred through the closure bands 253a, 253b, as will be discussed in greater detail below. Therefore, shifting of the horizontal bar 262 as a result of opposite movement of the closure bands 253a, 253b can allow precise and effective manipulation of the jaws 242, 244 by the closure mechanism 260 even when the end effector 240 is articulated.

Figure 4D:
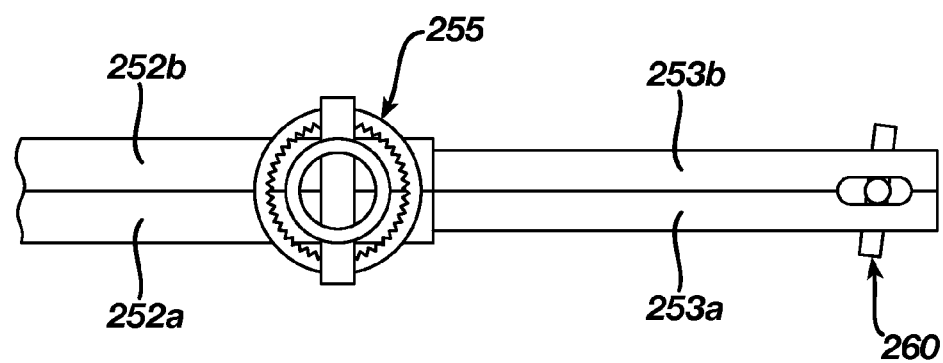
FIG. 4D is a top view showing the first and second closure bands of FIG. 4A extending from the support housing and through an articulation mechanism, and showing first and second articulation bands extending from the articulation mechanism.

FIG. 4D shows an embodiment of the electrosurgical instrument 200 having proximal ends of the first and second articulation bands 252a, 252b coupled to an articulation mechanism 255, and having the first and second closure bands 253a, 253b extending through the articulation mechanism 255 and having proximal ends coupled to the closure mechanism 260. The articulation mechanism 255 can assist with moving one or both of the articulation bands 252a, 252b in order to articulate the end effector, such as described above. In addition, the closure mechanism 260 can assist with translating the closure bands 253a, 253b in order to open and close the jaws 242, 244 even when the end effector is articulated, such as also describe above. Although a configuration of the closure bands 253a, 253b relative to the articulation bands 252a, 252b is shown in FIG. 4D, any number of configurations can be included in the electrosurgical instrument.

Figure 5A:
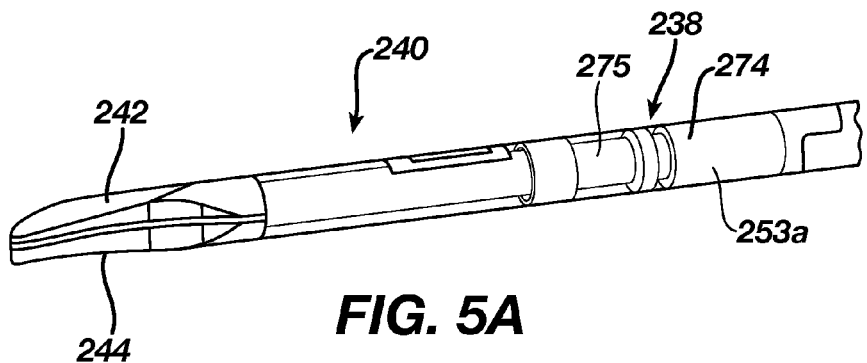
FIG. 5A is a side perspective view of the distal end of the electrosurgical instrument shown in FIG. 2A with the proximal pull tube shown in a proximal position, which forces the jaws into a closed configuration.
Figure 5B:
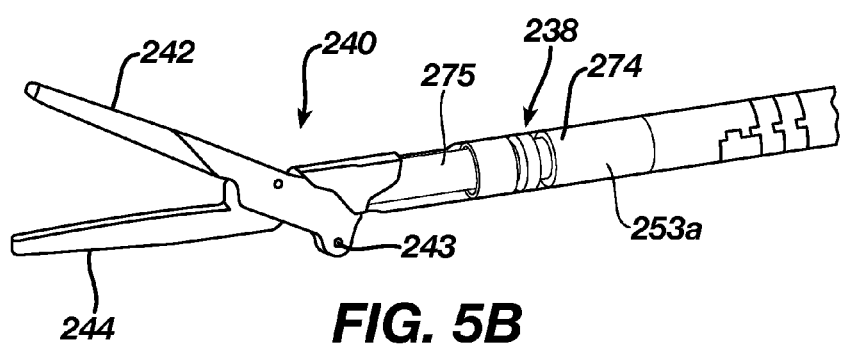
FIG. 5B is a side perspective view of the distal end of the electrosurgical instrument shown in FIG. 5A with the proximal pull tube shown in a distal position, which forces the jaws into an open configuration.

As shown in FIGS. 4A and 5A-5C, a distal end 272 of the closure bands 253a, 253b can be coupled to a proximal pull tube 274, which can be operatively coupled to the first jaw 242. For example, translation of the closure bands 253a, 253b in the distal direction, such as from distal translation of the closure mechanism 260 relative to the shaft 230, can cause the proximal pull tube 274 to translate in the distal direction relative to the shaft 230. Translation of the proximal pull tube 274 in the distal direction relative to the shaft 230 can cause the jaws 244, 242 to open, as shown in FIG. 5B, and as will be described in greater detail below. In addition, translation of the proximal pull tube 274 in the proximal direction relative to the shaft 230 can cause the jaws 242, 244 to close, as shown in FIG. 5A, and as will also be described in greater detail below.

Figure 5C:
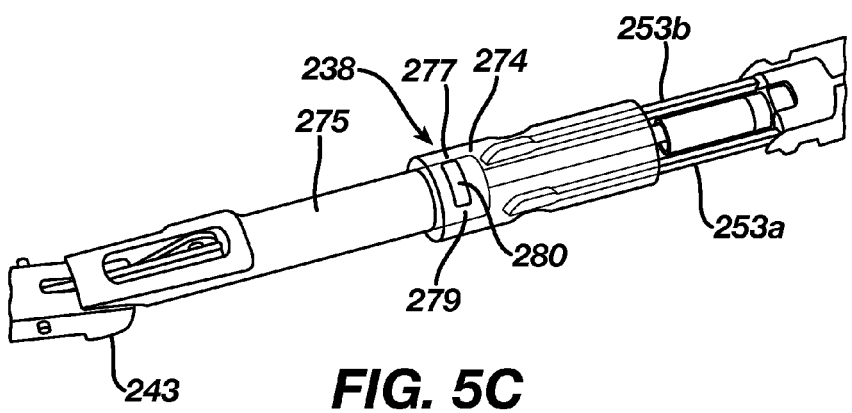
FIG. 5C is a side perspective view of a rotational joint of the electrosurgical instrument shown in FIG. 2A showing the proximal tube rotatably coupled to a distal pull tube that is operatively coupled to the jaws.

The proximal pull tube 274 can be cylindrical in shape and can slidably translate along an inner wall of the shaft 230. As shown in FIG. 5C, the closure bands 253a, 253b can be coupled at or adjacent a proximal end of the proximal pull tube 274. In addition, a distal end of the proximal pull tube 274 can be rotatably coupled to a distal pull tube 275, which can also have a cylindrical shape. This rotatable coupling between the proximal pull tube 274 and the distal pull tube 275 can form a part of the rotational joint 238. As such, the proximal pull tube 274 can be configured to linearly translate and the distal pull tube 275 can be configured to linearly translate along with the proximal pull tube 274. In addition, the distal pull tube 275 can be configured to rotate independently from the proximal pull tube 274. This allows the end effector to be rotated without rotating the closure bands 253a, 253b coupled to the proximal pull tube 274.

In one embodiment, the rotational joint 238 can include a slotted passageway 277 that extends a distance around a circumference of the distal end of the proximal pull tube 274, a circumferential recess 279 that extends at least partially around the proximal end of the distal pull tube 275, and at least one coupling pin 280. The slotted passageway 277 can align with the circumferential recess 279, which can allow the coupling pin 280 to engage both the slotted passageway 277 and circumferential recess 279 in order to rotatably couple the proximal pull tube 274 to the distal pull tube 275. In this configuration, the distal pull tube 275 can rotate relative to the proximal pull tube 274, such as by allowing the coupling pin 280 to circumferentially translate along the circumferential recess 279 as the distal pull tube 275 rotates relative to the proximal pull tube 274. In addition, this configuration allows simultaneous linear translation of the proximal pull tube 274 and distal pull tube 275 in either the proximal or distal direction relative to the shaft 230.

The distal pull tube 275 can be operatively coupled to the pivotal coupling 243 that can allow the first jaw 242 to pivot relative to the second jaw 244 (i.e., open and close the jaws 242, 244). For example, linear translation of the distal pull tube 275 in the distal direction can activate the pivotal coupling 243 and cause the first jaw 242 to pivot into an open configuration relative to the second jaw 244. In addition, linear translation of the distal pull tube 275 in the proximal direction can activate the pivotal coupling 243 and cause the first jaw 242 to pivot into a closed configuration relative to the second jaw 244. Linear translation of the distal pull tube 275 can be caused by pushing or pulling of the closure bands 253a, 253b relative to the proximal pull tube 274, which is coupled to the distal pull tube 275. Additionally, rotation of the distal pull tube 275 or any part of the end effector can be caused by rotation of the knife 282, as will be discussed in greater detail below.

Figure 6:
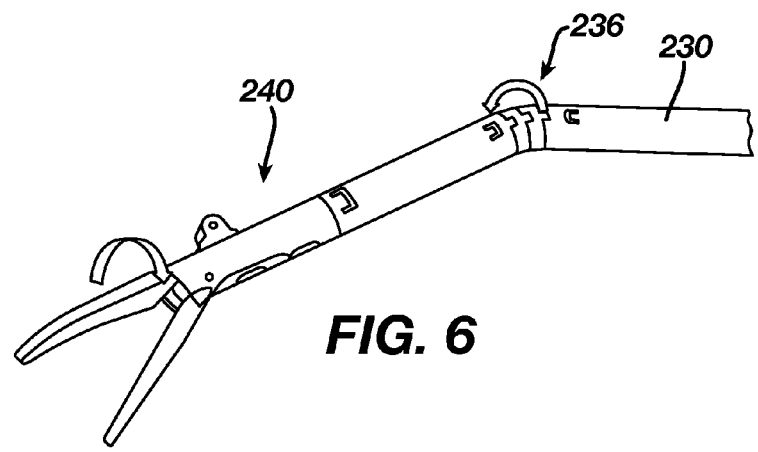
FIG. 6 is a side perspective view of the electrosurgical instrument of FIG. 2A showing simultaneous articulation of the shaft and rotation of the end effector.

As shown in FIG. 6, both articulation and rotation of the end effector 240 can occur either independently or simultaneously. Furthermore, opening and closing of the jaws 242, 244 can occur either independently or simultaneously with articulation and/or rotation of the end effector 240.

Figure 7A:
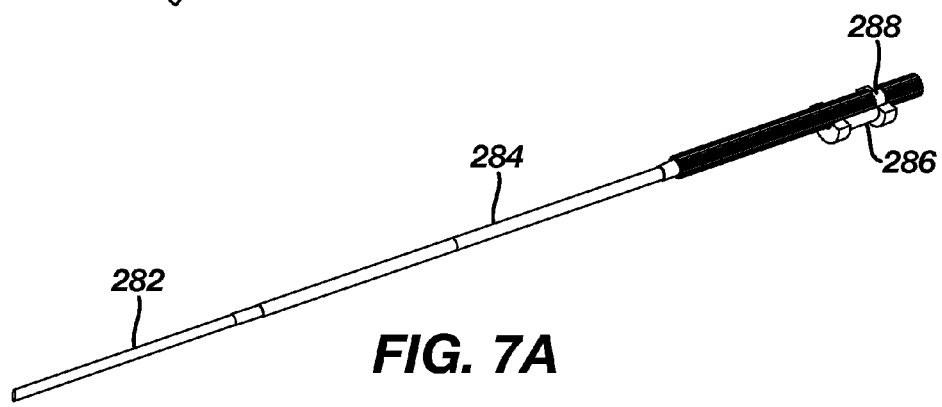
FIG. 7A is a side perspective view of a part of the knife translating and rotating mechanism of the electrosurgical instrument shown in FIG. 2A, including a knife positioned at a distal end of a knife positioning rod and a knife advancing member positioned along a proximal end of the knife positioning rod.
Figure 7B:
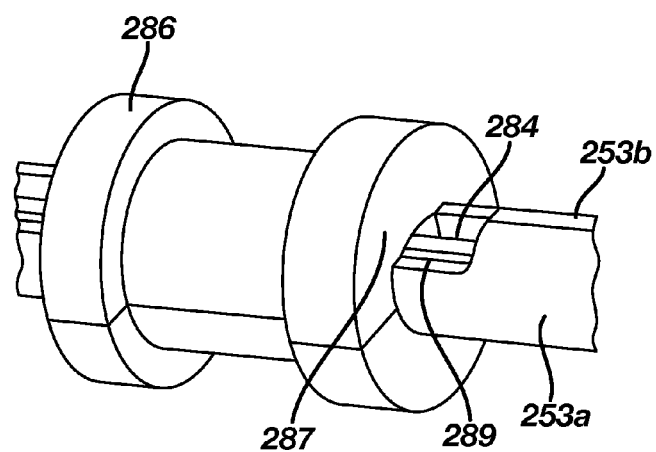
FIG. 7B is a side perspective view of the knife advancing member shown in FIG. 7A engaged with a slot formed in the knife positioning rod.

FIGS. 7A and 7B show a part of the knife advancing and rotating mechanism, which can include a knife 282 positioned at a distal end of a knife positioning rod 284. In addition, a knife advancing member 286 can be coupled to the knife positioning rod 284. The knife advancing member 286 can be cylindrical in shape with a central passageway and it can include a rod engaging feature 287 that can engage and secure the positioning of the knife advancing member 286 relative to the knife positioning rod 284. For example, the knife positioning rod 284 can include a circumferential slot 288 that can accept the rod engaging feature 287 of the knife advancing member 286. This can prevent at least translational movement of the knife advancing member 286 relative to the knife positioning rod 284 (such that the two components can translate together), while allowing rotational movement of the knife positioning rod 284 relative to the knife advancing member 286 (e.g., by allowing the rod engaging feature 287 to travel along the circumferential slot 288 as the knife positioning rod 284 rotates relative to the knife advancing member 286).

The rod engaging feature 287 can include an extension along a part of the central passageway of the knife advancing member 286. For example, the extension forming the rod engaging feature 287 can cause the part of the central passageway to be asymmetrical and allow the rod engaging feature 287 to engage the circumferential slot 288, thereby securing the knife advancing member 286 relative to the knife positioning rod 284. In addition, the knife advancing member 286 can be non-rotatable relative to the shaft 230. For example, an opening 289 formed between the closure bands 253a, 253b can allow the rod engaging feature 287 to extend past the closure bands 253a, 253b and engage the circumferential slot 288, which can allow the knife advancing member 286 to translate along the opening 289 while also preventing rotational movement of the knife advancing member 286 relative to the closure bands 253a, 253b (e.g., due to the opening 289 preventing rotational movement of the rod engaging feature 287 extending therethrough).

The engagement between the knife advancing member 286 and the knife positioning rod 284 can allow longitudinal translation of the knife advancing member 286 to cause simultaneous longitudinal translation of the knife positioning rod 284 and knife 282 in either the proximal or distal direction relative to the shaft 230. For example, proximal translation of the knife advancing member 286 can cause proximal translation of the knife 282 into and along a part of the end effector 240, such as in order to cut tissue captured between the jaws 242, 244. Actuating a firing member on the handpiece (not shown) can cause the non-rotatable knife advancing member 286 to axially translate to advance the knife 282 along the end effector in order to thereby cut tissue captured between the jaws 242, 244.

Figure 7C:
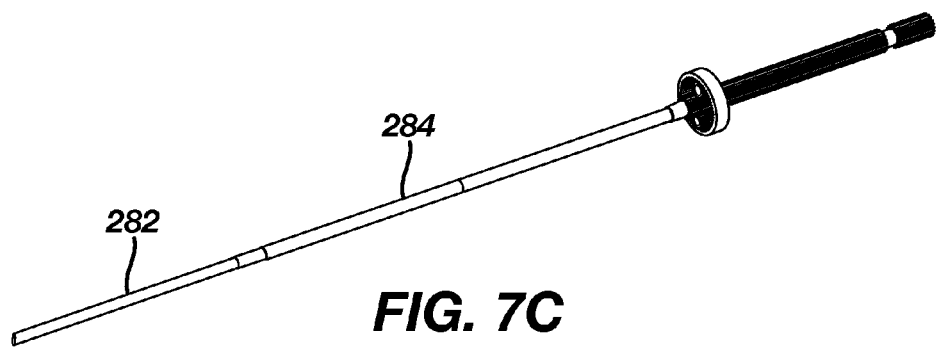
FIG. 7C is a side perspective view of a part of the knife advancing and rotating mechanism of the electrosurgical instrument shown in FIG. 2A, including a knife rotating member positioned along the knife positioning rod.
Figure 7D:
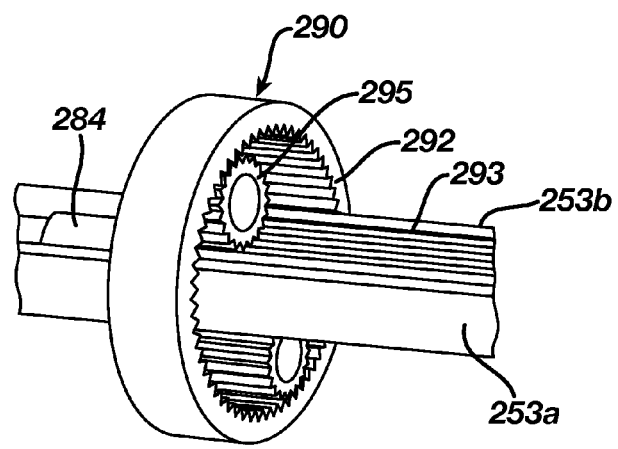
FIG. 7D is a side perspective view of the knife rotating member shown in FIG. 6C engaged with positioning rod surface features formed along a length of the knife positioning rod.

FIGS. 7C and 7D show additional parts of the knife advancing and rotating mechanism, which can include a knife rotating member 290 coupled to the knife positioning rod 284. The knife rotating member 290 can have a hollow wheel configuration that is rotatable about a central axis. The knife rotating member 290 can include first surface features 292 along an inner wall that engage with a gear 295 configured to engage with positioning rod surface features 293 formed along a part of the knife positioning rod 284. As such, when the knife rotating member 290 is rotated relative to the shaft 230 (e.g., by an actuator on the handpiece 20), the gear 295 is forced to rotate, which causes rotation of the knife positioning rod 284. Rotation of the knife positioning rod 284 can cause rotation of the knife 282, which is coupled to a part of the end effector 240 such that rotation of the knife 282 causes simultaneous rotation of the end effector 240.

The positioning rod surface features 293 can include elongated grooves extending along a length of the knife positioning rod 284. In addition, the gear 295 can include the same or similar features, such as elongated grooves or teeth, which can allow rotation of the gear 295 to cause rotation of the knife positioning rod 284. However, any number of features and configurations can be included to cause the knife positioning rod 284 to rotate and thereby cause the end effector 240 to simultaneously rotate.

Figure 8A:
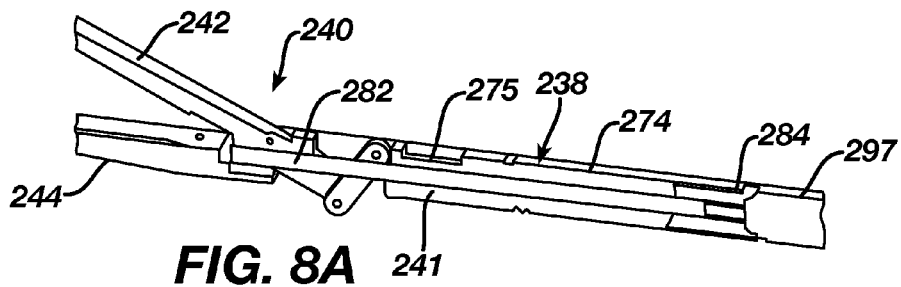
FIG. 8A is a cross-sectional view of a part of the electrosurgical instrument shown in FIG. 2A, which shows the rotational joint and the knife extending through a passageway in the end effector.

FIG. 8A-8D illustrate features of the electrosurgical instrument that can allow the knife 282 to translate and rotate, including during articulation of the shaft 230, as well as features that allow rotation of the knife 282 to cause rotation of the end effector 240. For example, FIG. 8A shows the knife 282 extending through a passageway 241 of the end effector 240. The passageway 241 can be configured such that it allows translation of the knife 282 relative to the end effector 240, but does not allow rotation of the knife 282 relative to the end effector 240 such that the two components can rotate as a unit. For example, the passageway 241 can be non-symmetrical or square shaped, which can prevent rotation of the knife 282 within the passageway 241 while allowing translation.

Figure 8B:
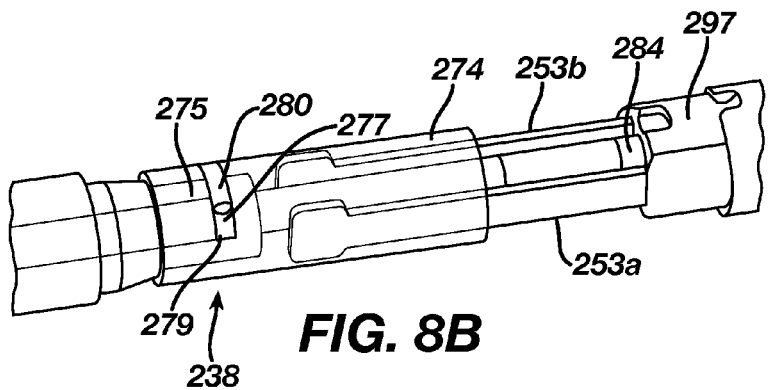
FIG. 8B is a side perspective view of the rotational joint of the electrosurgical instrument shown in FIG. 8A.
Figure 8C:
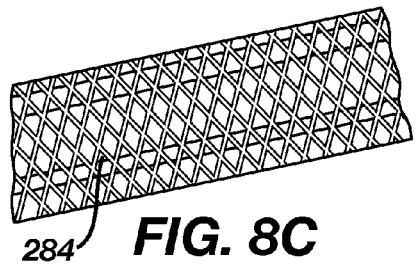
FIG. 8C is a side perspective view of a knife positioning rod that positions the knife shown in FIG. 8A, the knife positioning rod including a flexible braided tube.

As shown in FIGS. 8B and 8C, at least a part of the knife positioning rod 284 can be made out of a flexible material, such as braided tubing, which can allow the knife positioning rod 284 to bend at least along the articulation section 236. In addition, the flexible material of the knife positioning rod 284 can also have sufficient structural rigidity to cause advancement and retraction of the knife 282 relative to the end effector 240.

Figure 8D:
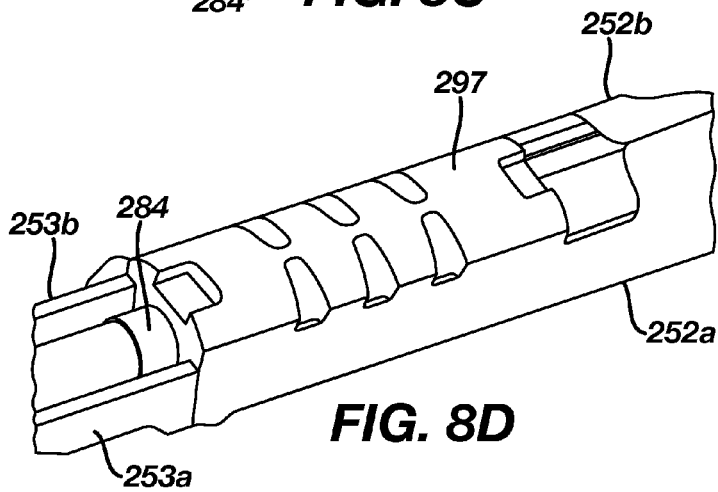
FIG. 8D is a side perspective view of a protective spacer shown in FIG. 8A, which is configured to extend between the articulation bands and knife positioning rod.

As shown in FIG. 8D, a protective spacer 297 can extend along a part of the knife positioning rod 284, such as along the articulation section 236, in order to ensure separation of the articulating bands 252a, 252b and the closure bands 253a, 253b from the knife positioning rod 284. The articulating bands 252a, 252b and closure bands 253a, 253b can extend along an outer surface of the protective spacer 297 and the knife positioning rod 284 can extend along a passageway extending through the protective spacer 297. The protective spacer 297 can have a cylindrical shape and can include cutouts along its length to improve flexibility of the protective spacer 297. For example, the protective spacer 297 can be positioned within a part of the articulation section 236 and can bend or articulate in response to articulation of the shaft 230.

Figure 9A:
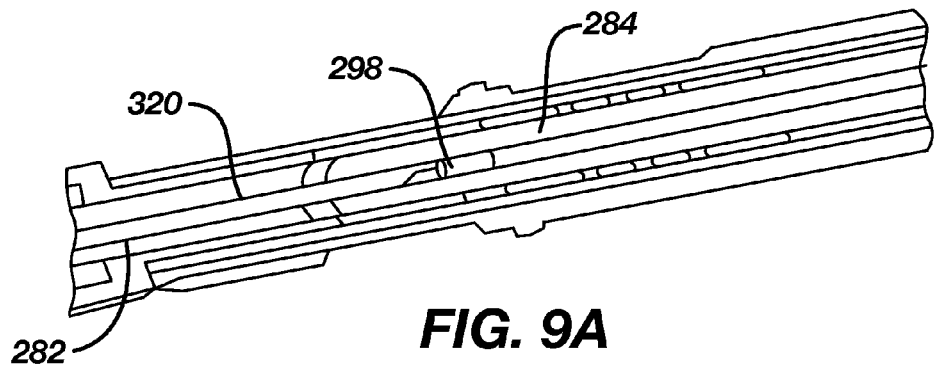
FIG. 9A is a side perspective view of an active rod that extends along the shaft of the electrosurgical instrument of FIG. 2A and can provide electrical energy for performing electrosurgical procedures.
Figure 9B:
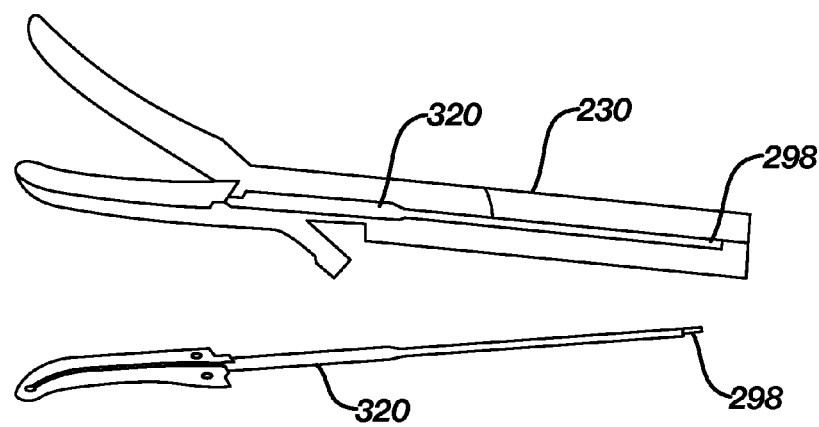
FIG. 9B includes side perspective views of a coated electrode that is in electrical communication with the active rod shown in FIG. 9A.
Figure 9C:
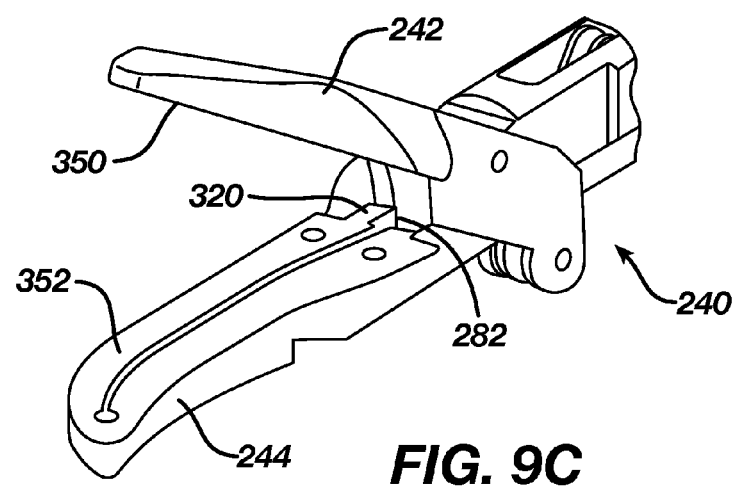
FIG. 9C is a side perspective view of the end effector of the electrosurgical instrument of FIG. 2A showing the coated electrode shown in FIG. 9B extending along the end effector.

FIGS. 9A-9C illustrate features for transmitting electrical energy through the electrosurgical instrument, such as for performing electrosurgical procedures with the electrosurgical instrument 200. For example, FIG. 9A shows an active rod 298 that can extend along the shaft 230, including within and along at least a part of the knife positioning rod 284. The active rod 298 can be in electrical communication with a power source at a proximal end and a coated electrode 320 (e.g., ceramic coated) at a distal end, as shown in FIG. 9B. The coated electrode 320 can be insulated in order to protect the electrode from other metal parts of the electrosurgical instrument 200. The coated electrode 320 can extend along a part of the end effector 240, such as along the second jaw 244 as shown in FIG. 9C. For example, activation of the active rod 298 (e.g., providing an electric current) can allow the coated electrode 320 to assist with cutting, coagulating, desiccating and/or fulgurating tissue.

For example, the first jaw 242 can include a first electrode surface 350 and the second jaw 244 can include a second electrode surface 352. Electrode surfaces 350, 352 can be in communication with the active rod 298 that extends along a length of shaft 230 and is in communication with an electrical source (not shown). The electrical source can be operable to deliver RF energy to the first electrode surface 350 at a first polarity and to the second electrode surface 352 at a second (opposite) polarity, such that RF current flows between electrode surfaces 350, 352 and thereby through tissue captured between jaws 242, 244. The electrical source may be external to electrosurgical instrument 200 or may be integral with electrosurgical instrument 200 (e.g., in handpiece, etc.), as described in one or more references cited herein or otherwise.

FIGS. 10A-10E illustrate another embodiment of a shaft 330 of an electrosurgical instrument, which includes a sheath 310 that can be translated along an outer surface of the shaft 330 and which can affect the bending radius formed during articulation of the shaft 330, such as along the articulation section 336. The sheath 310 can be in the form of an elongated tubular body that can be slidably engaged with the outer surface of the shaft 330. FIG. 10A shows the shaft 330 in a straight configuration, such as prior to being articulated. FIG. 10B shows the shaft 330 articulated without the sheath 310 positioned over a part of the articulation section 336. FIG. 10C shows the shaft 330 articulated with the sheath 310 positioned over a proximal part of the articulation section 336. FIG. 10D shows the shaft 330 articulated with the sheath 310 positioned over a distal part of the articulation section 336. As shown in at least FIGS. 10B-10D, positioning of the sheath 310 relative to the articulation section 336 during articulation of the shaft 330 can provide various shapes and bending radii of the shaft 330, which can assist with navigation of the electrosurgical instrument. Positioning of the sheath 310 can be done by a user, such as by the user sliding the sheath 310 along the shaft to a desired position along the shaft 330. Additionally, positioning of the sheath 310 can be done prior to insertion of the shaft 330 through an incision of a patient.

As shown in FIG. 10E, in certain embodiments the sheath 310 can include a detent feature 312 that can engage surface features 314 positioned along a length of the shaft 330, such as along the articulation section 336. The engagement between the detent feature 312 and the surface features 314 can assist with securing the positioning of the sheath 310 relative to the shaft 330 and control the bending radius of the articulation section 336. The detent feature 312 can include at least one indent along the length of the sheath 310; however, the detent feature can include any number of features for assisting in securing the positioning of the sheath 310 relative to the shaft 330. For example, positioning of the sheath 310 can be done by a user, such as prior to inserting the shaft 330 through an incision of a patient.

Figure 11:
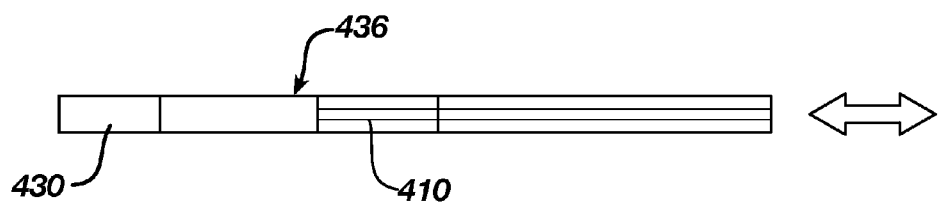
FIG. 11 is a side view of another embodiment of a shaft of an electrosurgical instrument in a straight configuration, with the shaft including rigid members extending within the shaft that can be longitudinally translated in order to vary the articulation angle formed along an articulation section of the shaft.

FIG. 11 illustrates another embodiment of a shaft 430 of an electrosurgical instrument, which includes at least one rigid member 410 that can be longitudinally translated along an inner surface of the shaft 430 and which can affect the bending radius formed during articulation of the shaft 430, such as along the articulation section 436. For example, translational movement of the rigid members 410 can be controlled from the handpiece. In some embodiments, distal translation of the rigid members 410 can decrease the bending radius of the shaft when articulated and proximal translation of the rigid members 410 can increase the bending radius of the shaft 430 when articulated.

Figure 12A:
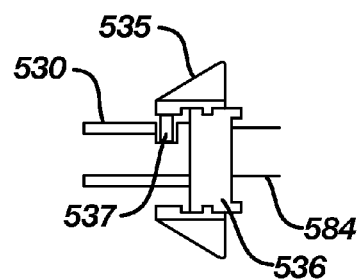
FIG. 12A is a cross-sectional view of another embodiment of a shaft of an electrosurgical instrument including a knob that can assist with rotating a component positioned within the shaft, such as a knife positioning rod.
Figure 12B:
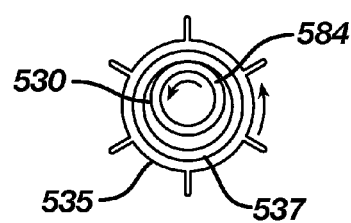
FIG. 12B is a cross-sectional view of the knob shown in FIG. 12A rotating and causing the knife positioning rod to rotate in the same direction.
Figure 12C:
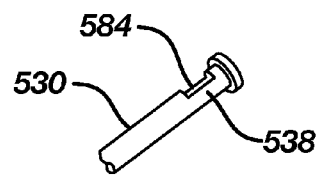
FIG. 12C is a side perspective view of the shaft shown in FIG. 12A having an opening for allowing the knob to contact the knife positioning rod.

FIGS. 12A-12C illustrate another embodiment of a shaft 530 of an electrosurgical instrument including a rotating knob 535 that can assist with rotating a component positioned within the shaft 530 (e.g., a knife positioning rod 584) without requiring rotation of the outer shaft 530. The rotating knob 535 can have a generally cylindrical shape with a through-hole 536 that passes along a longitudinal axis of the rotating knob 535. The through-hole 536 can have a diameter that is greater than the outer diameter of the shaft 530 and that can be coupled to a shroud 539 that is fixed to an outer surface of the shaft 530 for assisting in the positioning of the rotating knob 535 relative to the shaft 530. The coupling between the rotating knob 535 and shroud 539 allows the rotating knob 535 to rotate relative to the shroud 539 and shaft 530.

The shroud 539 can be generally cylindrical in shape and can be coupled to the shaft 530 such that a central longitudinal axis of the shroud 539 is parallel and offset from a central longitudinal axis of the shaft 530. This offset can allow a part of the rotating knob 535, such as a contact point 537, to contact a part of the shaft or a component positioned within the shaft, such as the knife positioning rod 584. In addition, this contact can allow rotation of the rotating knob 535 to cause rotation of the part of the shaft 530 or component within the shaft 530. The contact point 537 can include a higher friction material (e.g., rubber) in order to improve rotation of the shaft 530 or component positioned within the shaft as a result of rotation of the rotating knob 535. The contact point 537 can include a circumferential extension that extends along an inner wall of the rotating knob 535, as shown in FIG. 12A.

For example, as show in FIGS. 12A-12C, the rotating knob 535 can be rotatably coupled to the shroud 539, which is fixed to the shaft 530. In addition, the shroud 539 can be offset from the shaft 530, which can allow the contact point 537 of the rotating knob 535 to contact a part of the knife positioning rod 584. The shaft 530 can include an opening 538, as shown in FIG. 12C, that can allow the contact point 537 to extend through the shaft 530 in order to contact the knife positioning rod 584. As such, rotation of the rotating knob 535 in a first direction can force the knife positioning rod 584 to also rotate in the first direction, as shown in FIG. 12B. This can allow the knife positioning rod 584, including a knife coupled to a distal end of the knife positioning rod 584, to rotate independently and relative to the shaft 530.

Various methods for treating tissue are also provided. In one embodiment, the end effector 240 of the electrosurgical device 200 can be inserted into a patient via a trocar. The articulation section 236 can be substantially straight when the end effector 240 and part of the shaft 230 are inserted through the trocar or other access device. Articulation of the end effector 240 can be controlled by the handpiece (such as the handpiece 20 in FIG. 1), which can cause the end effector 240 to be positioned at a desired position and orientation relative to an anatomical structure within the patient. As described above, articulation of the end effector 240 can be caused by either pushing or pulling on one or more of the articulation bands 252a, 252b extending through the shaft 230. For example, pushing on the first articulation band 252a and pulling on the opposing second articulation band 252b can cause the end effector 240 to move in a direction toward a side having articulation band 252b extending therealong.

In addition, opening and closing of the jaws 242, 244 can be controlled by the handpiece. As also described above, the opening and closing of the jaws 242, 244 can be caused by linear translation of the distal pull tube 275. For example, linear translation of the distal pull tube 275 in the distal direction can activate the pivotal coupling 243 and cause the first jaw 242 to pivot into an open configuration relative to the second jaw 244. In addition, linear translation of the distal pull tube 275 in the proximal direction can activate the pivotal coupling 243 and cause the first jaw 242 to pivot into a closed configuration relative to the second jaw 244. Linear translation of the distal pull tube 275 can be caused by pushing or pulling of the closure bands 253a, 253b relative to the proximal pull tube 274, which is coupled to the distal pull tube 275.

Additionally, translational movement of the knife 282 can be controlled by the handpiece. Translational movement of the knife, as described above, can be caused by longitudinal translation of the knife advancing member 286, which can cause simultaneous longitudinal translation of the knife positioning rod 284 and knife 282 in either the proximal or distal direction relative to the shaft 230. For example, proximal translation of the knife advancing member 286 can cause proximal translation of the knife 282 into and along a part of the end effector 240, such as in order to cut tissue captured between the jaws 242, 244.

Furthermore, rotation of the end effector 240, including the knife 282, can be controlled by the handpiece. Rotational movement of the end effector 240, as also described above, can be caused by rotational movement of the knife rotating member 290. For example, the knife rotating member can be rotated relative to the shaft 230 (e.g., by an actuator on the handpiece 20), which can force the gear 295 to rotate. Rotation of the gear 295 can cause rotation of the knife positioning rod 284, which can then cause rotation of the knife 282. The knife 282 can be coupled to a part of the end effector 240 such that rotation of the knife 282 causes simultaneous rotation of the end effector 240.

Two layers of tissue of an anatomical structure can be captured between the jaws 242, 244 (e.g., by squeezing trigger 24 toward pistol grip 22 of handpiece 20). Such layers of tissue may be part of the same natural lumen defining an anatomical structure (e.g., blood vessel, portion of gastrointestinal tract, portion of reproductive system, etc.) in a patient. For instance, one tissue layer can include the top portion of a blood vessel while the other tissue layer can include the bottom portion of the blood vessel, along the same region of length of the blood vessel (e.g., such that the fluid path through the blood vessel before use of electrosurgical instrument 200 is perpendicular to the longitudinal axis defined by end effector 240, etc.). In other words, the lengths of the jaws 242, 244 may be oriented perpendicular to (or at least generally transverse to) the length of the blood vessel.

With tissue layers captured between the jaws 242, 244, the knife 282 can be distally advanced in order to cut the tissue, such as in a direction that is generally transverse to the length of the blood vessel. In addition, the electrode surfaces 350, 352 can be activated with bipolar RF energy. The bipolar RF energy delivered by power source can ultimately thermally weld the tissue layer portions together, including on either side of the severed tissue.

In certain circumstances, the heat generated by the activated electrode surfaces 350, 352 can denature the collagen within the tissue layer portions and, in cooperation with clamping pressure provided by the jaws 242, 244, the denatured collagen can form a seal within the tissue layer portions. Thus, the severed ends of the natural lumen defining anatomical structure are hemostatically sealed shut, such that the severed ends will not leak bodily fluids.

The devices and methods disclosed herein can be used in minimally-invasive surgery and/or open surgery. While the devices and methods disclosed herein are generally described in the context of laparoscopic procedures, it will be appreciated that the methods and devices disclosed herein can be used with any human or animal tissue, implant, non-living object, and so forth.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. An electrosurgical device, comprising:
   a handle assembly;
   an elongate shaft extending distally from the handle assembly and having an end effector with opposed jaws rotatably coupled to a distal end thereof, the end effector being coupled to the elongate shaft at a rotational joint, the elongate shaft including an articulation joint proximal of the rotational joint for allowing articulation of the end effector relative to the elongate shaft; and
   a closure assembly having a support housing with first and second closure bands extending therethrough, the first and second closure bands extending through the elongate shaft and being operatively coupled to the end effector for moving the opposed jaws between open and closed positions, the support housing being configured to allow the first and second closure bands to shift axially relative to one another within the support housing in response to articulation of the end effector about the articulation joint, and with the first and second closure bands in any shifted position, the support housing being axially movable to simultaneously axially move the first and second closure bands and to cause the opposed jaws to move between the open and closed positions.

2. The device of claim 1, wherein the support housing comprises a gimbal having an axial opening extending longitudinally therethrough for receiving the first and second closure bands.

3. The device of claim 1, wherein the support housing includes vertical and horizontal cross bars disposed therein and coupled to one another, the vertical cross bar being configured to pivot to allow shifting movement of the first and second closure bands, and the horizontal cross bar being configured to move axially to simultaneously axially move with the first and second closure bands.

4. The device of claim 3, wherein the first and second closure bands each include an opening formed in a proximal end thereof, and the horizontal cross bar extends through the opening formed in each of the first and second closure bands.

5. The device of claim 4, wherein the support housing has opposed elongate slots formed therein for receiving opposed ends of the horizontal cross bar such that the opposed ends of the horizontal cross bar can pivot within the elongate slots.

6. The device of claim 4, wherein opposed ends of the vertical cross bar are fixedly disposed within opposed holes formed in the support housing.

7. The device of claim 1, further comprising an articulation assembly having an articulation mechanism that controls first and second articulation bands extending through the elongate shaft and operatively coupled to the end effector such that activation of the articulation mechanism causes axial movement of the first and second articulation bands, which is effective to articulate the end effector relative to the elongate shaft about the articulation joint.

8. The device of claim 7, wherein the articulation mechanism includes an articulation knob disposed on the handle assembly for causing axial movement of the first and second articulation bands.

9. The device of claim 1, further including an articulation control mechanism disposed along the elongate shaft and slidably movable relative to the articulation joint to adjust a bending radius of the articulation joint.

10. The device of claim 1, further including an active rod extending along the elongate shaft and configured to provide electrical communication between a power source at a proximal end of the active rod and an electrode at a distal end of the active rod.

11. The device of claim 10, wherein the electrode extends along a length of a first jaw of the opposed jaws.

12. An electrosurgical device, comprising:
    an elongate shaft having an end effector with opposed jaws rotatably coupled to a distal end thereof, the end effector being coupled to the elongate shaft at a rotational joint, the elongate shaft including an articulation joint proximal of the rotational joint for allowing articulation of the end effector relative to the elongate shaft;
    a knife assembly coupled to the end effector and including a knife at a distal end thereof configured to axially translate relative to the opposed jaws for cutting tissue engaged between the opposed jaws;
    a knife positioning rod extending through the elongate shaft and coupled to the knife assembly, the knife positioning rod being axially translatable for causing the knife assembly to translate, and the knife positioning rod being rotatable relative to the elongate shaft to cause rotation of the end effector about the rotational joint; and
    a knife advancing member coupled to the knife positioning rod for causing axial translation of the knife positioning rod relative to the elongate shaft, the knife advancing member being non-rotatable relative to the elongate shaft and allowing free rotational movement of the knife positioning rod relative thereto.

13. The device of claim 12, wherein the knife positioning rod includes a cut-out formed therein for receiving a portion of the knife advancing member such that the knife advancing member is effective to cause axial translation of the knife positioning rod while allowing free rotational movement of the knife advancer shaft relative thereto.

14. The device of claim 12, further comprising a knife rotating member coupled to the knife positioning rod, the knife rotating member being axially rotatable relative to the elongate shaft to cause rotation of the end effector about the rotational joint.

15. The device of claim 12, wherein at least a portion of the knife positioning rod is formed from a flexible braided tubing.

16. The device of claim 12, further including an active rod extending along the elongate shaft and configured to provide electrical communication between a power source at a proximal end of the active rod and an electrode at a distal end of the active rod.

17. The device of claim 16, wherein the electrode extends along a length of a first jaw of the opposed jaws.

18. An electrosurgical device, comprising:
an elongate shaft having an end effector with opposed jaws rotatably coupled to a distal end thereof, the end effector being coupled to the elongate shaft at a rotational joint, the elongate shaft including an articulation joint proximal of the rotational joint for allowing articulation of the end effector relative to the elongate shaft;
a proximal pull tube extending through the elongate shaft proximal of the rotational joint, and a distal pull tube extending through the end effector only distal of the rotational joint, the proximal pull tube being axially translatable along the elongate shaft to cause the distal pull tube to axially translate to open and close the opposed jaws, and the distal pull tube being configured to rotate freely relative to the proximal pull tube to allow rotation of the end effector about the rotational joint.

19. The device of claim 18, further comprising a knife assembly extending through the end effector and including a knife for cutting tissue engaged between the opposed jaws, wherein rotation of the knife assembly is effective to cause rotation of the end effector about the rotational joint and to cause rotation of the distal pull tube relative to the proximal pull tube.

20. The device of claim 19, wherein the knife assembly includes a knife rotating member extending through the elongate shaft and coupled to a knife positioning rod having the knife positioned at a distal end thereof, the knife rotating member being axially rotatable relative to the elongate shaft to cause rotation of the knife assembly and end effector.

* * * * *